United States Patent [19]

Wernick et al.

[11] 4,426,292
[45] Jan. 17, 1984

[54] PROCESS FOR SELECTIVE SEPARATION OF MOLECULAR SPECIES FROM MIXTURES THEREOF USING CYCLODEXTRINS

[75] Inventors: David L. Wernick, Elizabeth; Stephen Scypinski, Garwood, both of N.J.

[73] Assignee: Exxon Research and Engineering Co., Florham Park, N.J.

[21] Appl. No.: 350,194

[22] Filed: Feb. 19, 1982

[51] Int. Cl.$^3$ .............................................. B01D 15/08
[52] U.S. Cl. .................................. 210/635; 210/670; 210/502.1; 55/67; 55/66; 55/74
[58] Field of Search ............ 210/635, 636, 670, 198.2, 210/502; 55/67, 386, 387, 389, 66, 74

[56] References Cited

U.S. PATENT DOCUMENTS 3,472,835 10/1969 Buckler et al. .................. 260/209

FOREIGN PATENT DOCUMENTS 50-96530 7/1975 Japan .
50-151804 12/1975 Japan .
50-151827 12/1975 Japan .
50-151833 12/1975 Japan .
52-42825 4/1977 Japan .
2030574 4/1980 United Kingdom .

OTHER PUBLICATIONS

Chromatographic and Allied Methods by Mikes, John Wiley and Sons of New York, pp. 335-343 and 368 relied on, 1979.
E. Smolkova et al., *J. Chromatography*, 241, 3 (1982).
E. Smolkova-Keulemansova, *J. Chromatography*, 251, 17 (1982).
M. Benito Casu et al., *Carbohydrate Research*, 76, 59 (1979).
Y. Mizobuchi, et al., *J. Chromatogr.*, 208, 35 (1981).
J. Szejtli, *Staerke*, 30, 127 (1978).
B. Siegel et al., *J.A.C.S.*, 97, 6869 (1975).
H. Schlenk et al., *J.A.C.S.*, 83, 2312 (1961).
G. Phillips et al., *J. Chem. Soc.*, 387, (1966).
J. Szejtli et al., *Acta Chim. Acad. Sci., Hung.*, 101, 27 (1979).
J. Szejtli et al., *Acta Chim. Acad. Sci., Hung.*, 94, 383 (1977).
M. Maciejewski et al., *J. Macromol. Sci. Chem.*, A13, 87 (1979).
D. French, PhD Thesis, Iowa State Univ. (1942).
H. Schlenk et al., *J.A.C.S.*, 77, 3587 (1955).
CPC International Product Brochure "Beta-Cyclodixtrin", Englewood Cliffs, N.J. (1968).
T. Kuge et al., *Agr. Biol. Chem.*, 32, 753 (1968).
C. Lee, *Sepn. Sci. Technol.*, 16, 25 (1981).
C. Lee, *J. Appl. Polym. Sci.*, 26, 489 (1981).
D. Sand et al., *Anal. Chem.*, 33, 1624 (1961).
H. Schlenk et al., *Anal. Chem.*, 34, 1529 (1962).
Y. Mizobuchi et al., *Bull. Chem. Soc. Jpn.*, 54, 2487 (1981).
Y. Mizobuchi et al., *J. Chromatogr.*, 194, 153 (1980).
M. Tanaka et al., *J. Chromatogr.*, 219, 108 (1981).
F. R. Senti et al., in L. Mandelcorn, Ed., "Non Stoichiometric Compounds", Academic Press, N.Y., 1964, pp. 568-605.
D. W. Griffiths et al., Advances in Catalysts, 23, 209 (1973).
J. A. Thoma et al., in R. L. Whistler et al., Ed., "Starch: Chemistry and Technology", vol. I, Academic Press, N.Y., 1965, pp. 209-249.
D. French, Advan. Carbohydrate Chem., 12, 189 (1957).
M. L. Bender et al., "Cyclodextrin Chemistry", Springer-Verlag, N.Y., 1978.
W. Saenger, *Angew. Chem. Int. Ed., Engl.*, 19, 344 (1980).
W. Saenger, in B. Pullman, Ed., "Environmental Effects on Molecular Structure and Properties", Reidel, Dordrecht, Holland, 1976, pp. 265-305.
D. W. Breck, "Zeolite Molecular Sieves: Structure, Chemistry, and Use", Wiley, New York, 1974, p. 609.
B. Klar et al., *Acta Cryst.*, B36, 1154 (1980).

*Primary Examiner*—John Adee
*Attorney, Agent, or Firm*—Janet E. Hasak

[57] ABSTRACT

A mixture of two or more fluid molecular species is resolved into its compartment parts by a selective separation process whereby the mixture is contacted with a solid particulate monomeric cyclodextrin. On contact, at least one of the molecular species is selectively sorbed onto the cyclodextrin, and thereafter the species is desorbed from the cyclodextrin. In a preferred aspect, the species to be separated are organic compounds.

19 Claims, 11 Drawing Figures

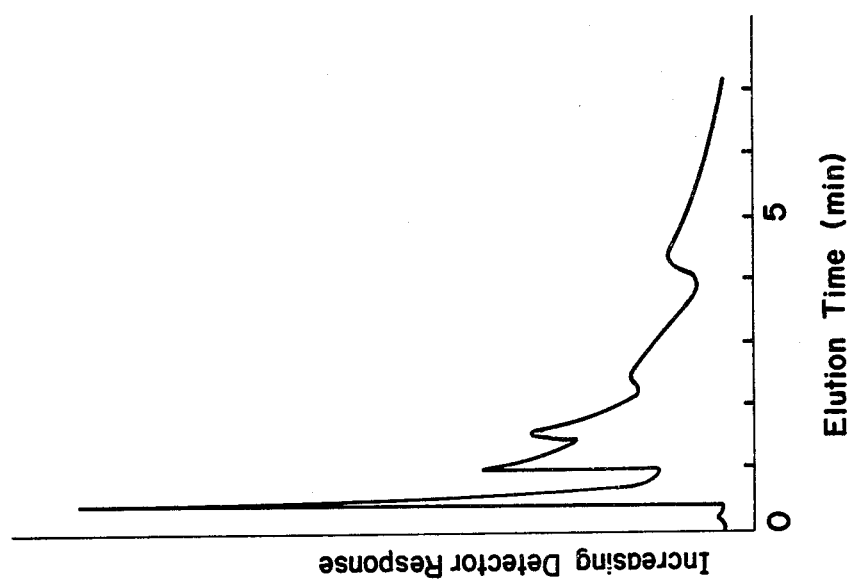
FIG. 7
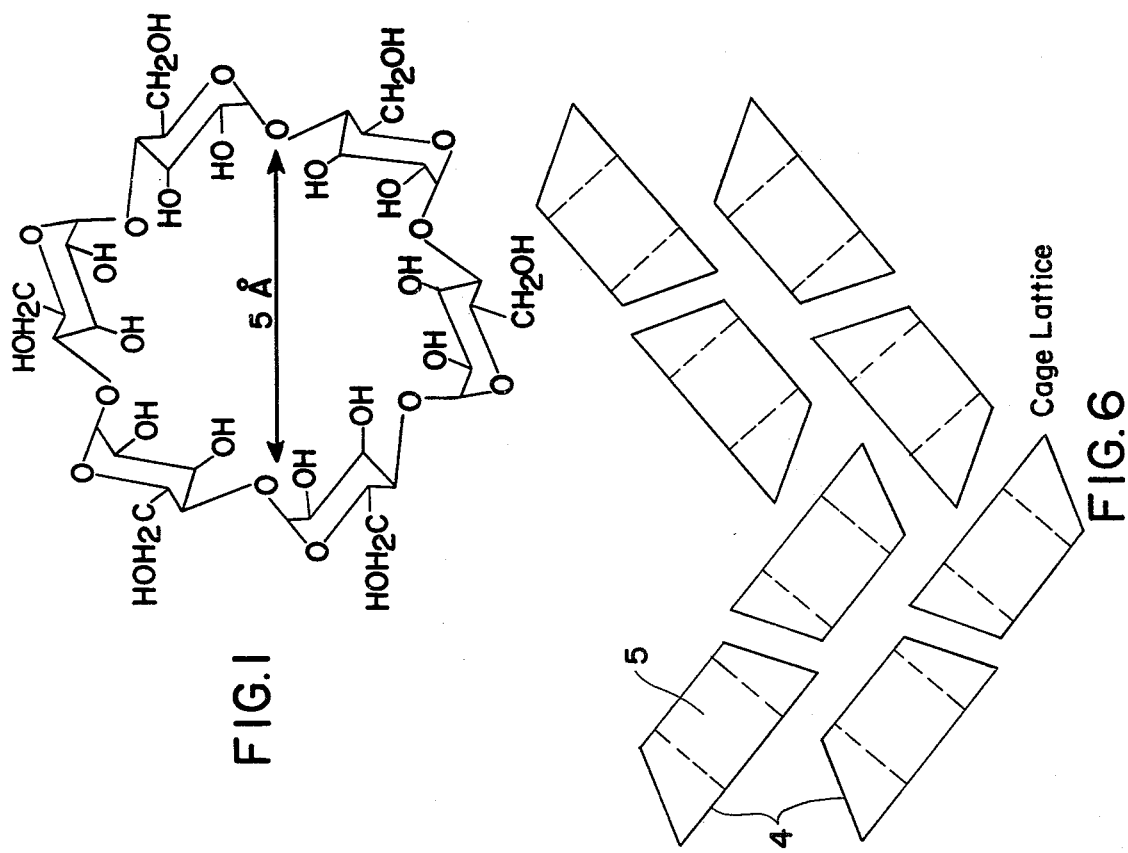
FIG. 1
FIG. 6

(Control)

(Control)

PROCESS FOR SELECTIVE SEPARATION OF MOLECULAR SPECIES FROM MIXTURES THEREOF USING CYCLODEXTRINS

BACKGROUND OF THE INVENTION

1. Field of the Invention:

The present invention relates to a process for selectively separating two or more fluid (liquid or gaseous) molecular species from a mixture thereof utilizing solid particulate monomeric cyclodextrin which functions as a reversible sorbent for at least one of the molecular species.

2. Description of Related Patents:

Many techniques are known for separating liquid and gaseous molecular components from mixtures thereof. Typical such separation techniques take into account the differences in one or more physical properties of the respective components such as boiling point, polarity, molecular size, and/or molecular shape. For example, distillation is known to effect separations primarily based on boiling point differences of the components. In gas chromatographic separation processes which employ, as a stationary phase, a sorbing material such as a porous organic polymer or an inert solid packing coated with an organic liquid, the components are separated by their respective affinities for the polymeric sorbent or liquid coating as well as by boiling point.

A particularly common method for separating components having similar structures involves use as adsorbents of a certain class of uncoated solid separating materials, namely, porous crystalline aluminosilicates otherwise known as zeolites, as described, for example, by M. N. Y. Lee, *Recent Developments in Separation Science* (N. Li, et al., ed.) Vol. I, "Novel Separation With Molecular Sieves Adsorption", CRC Press, Inc., Boca Raton, 1972, pp. 75–112.

While zeolites are useful in effecting selective separations of certain hydrocarbons and isomers, they are limited in several respects, notably in their ability to achieve separations of particular importance to the petroleum and chemical industries. Thus, for example, whereas several zeolite materials are effective for separating normal alkanes of small molecular diameter (e.g., about 4.5–5 Å) from other hydrocarbons, compounds of relatively large molecular size often cannot be separated by such zeolite materials. In addition, many zeolites are incapable of readily separating branched alkanes of similar structure from each other. Those separations which can be successfully carried out by using commercially available zeolites are strongly inhibited in the presence of water, so that care must be taken to avoid exposure of any part of the separation system to moisture during the separation process.

Cyclodextrins, which are cyclic oligosaccharides composed of alpha-1,4-linked glucose units arranged in a tours, are known to form inclusion complexes with a variety of "guest" molecules, i.e., molecules which are taken up by the "host" molecule, cyclodextrin. In addition, cyclodextrin and its derivatives are used to catalyze various homogeneous reactions and have been widely studied as models for enzyme catalysts.

Many of the cyclodextrin inclusion complexations observed in the past were conducted in aqueous or nonaqueous cyclodextrin solution. Thus, for example, Japanese Kokai Nos. 96530, 151804, 151827, 151833 and 2042825 disclose selective precipitation and separation of hydrocarbons with cyclodextrin solutions. Chromatographic separations by selective complexation of dissolved guests with insoluble, crosslinked cyclodextrin polymers in the presence of liquid water are disclosed in U.S. Pat. No. 3,472,835, U.K. Pat. No. 2,030,574 and by Y. Mizobuchi, et al., *J. Chromatogr.*, 208, 35 (1981) and J. Szejtli, *Staerke*, 30, 127 (1978). More recently, B. Siegel and R. Breslow, *J. Am. Chem. Soc.*, 97, 6869 (1975) reported that cyclodextrins form inclusion complexes in certain polar solvents such as dimethylsulfoxide.

It is known that guests can desorb from crystalline cyclodextrin complexes on washing with solvent, on heating or on allowing to stand, as reported by H. Schlenk and D. Sand., *J. Am. Chem. Soc.*, 83, 2312 (1961), G. Phillips and P. Baugh, *J. Chem. Soc.*, 387 (1966), J. Szejtli, et al., *Acta Chim. Acad. Sci. Hung.*, 101, 27 (1979); J. Szejtli and Z. Budai, *Acta Chim. Acad. Sci. Hung.*, 94, 383 (1977); and M. Maciejewski, et al., *J. Macromol. Sci. Chem.*, A13, 87 (1979). It is further known that crystalline cyclodextrins will sorb guests. D. French reports in his Ph.D. Thesis, Iowa State University, 1942, that only one of five crystal modifications of alpha-cyclodextrin complex, i.e., the one with a channel lattice structure, sorbed iodine vapor. H. Schlenk, et al., *J. Am. Chem. Soc.*, 77, 3587 (1955) discovered that alpha- and beta-cyclodextrins sorbed trichloroethylene and bromobenzene vapors, but only in the presence of water vapor or water of crystallization. A CPC International product information brochure entitled "Beta-Cyclodextrin", Englewood Cliffs, N.J., 1968 confirms Schlenk's work and concludes that water is necessary for appreciable cyclodextrin complexation. T. Kuge and K. Takeo, *Agr. Biol. Chem.*, 32, 753 (1968) report that several crystalline cyclodextrin inclusion complexes fail to sorb such compounds as toluene and butanol, but when beta-cyclodextrin. propanol complex is heated to vacuum, peak broadening on a gas chromatography column is observed. In addition, alterations in polymeric membrane selectivity and flux were observed by C. Lee., *Sepn. Sci. Technol.*, 16, 25 (1981) and *J. Appl. Polym. Sci.*, 26, 489 (1981) on addition of cyclodextrins to the aqueous membrane casting solution. This was explained as possibly due to selective diffusion of organic permeant through cyclodextrin channels.

U.S. Pat. No. 3,472,835 discloses use of solid crosslinked cyclodextrin polymers, which selectively sorb gas phase components of cigarette smoke or flavor components, to effect petroleum separations. Liquid acylcyclodextrins are reported by D. Sand, et al., *Anal. Chem.*, 33, 1624 (1961) and by H. Schlenk, et al., *Anal. Chem.*, 34, 1529 (1962) to separate fatty acid derivatives.

Recently, Y. Mizobuchi, et al., *J. Chromatogr.*, 194, 153 (1980) and Y. Mizobuchi, et al., *Bull Chem. Soc. Jpn.*, 54, 2487 (1981) disclose that cyclodextrin polyurethane resins, obtained by polymerization of cyclodextrins with diisocyanates, selectively sorb various organic compounds in the absence of solvent. The 1980 article further discloses that native beta-cyclodextrin reversibly sorbs benzene under similar conditions.

It has now been discovered that shape-selective separations of molecular species, especially organic compounds, from a mixture thereof can be achieved in a continuous or batch process by using monomeric cyclodextrin in the solid particulate form as a reversible sorbent for at least one of the components of the mixture.

The solid particulate cyclodextrins used herein are particularly suited for achieving separations for which zeolites are ineffective. For example, unlike zeolites, the monomeric solid particulate cyclodextrin is found to sorb guest molecules of much larger diameter than the crystallographically measured free diameter of the host molecule cavity. In addition, effective separation of olefins and of branched alkanes can be carried out by the process herein.

SUMMARY OF THE INVENTION

The present invention is directed to a process for selectively separating two or more fluid molecular species from a mixture containing the same comprising: (1) contacting said mixture with a solid particulate monomeric cyclodextrin, (2) sorbing at least one molecular species selectively on said solid cyclodextrin, and (3) desorbing said sorbed molecular species, thereby partially or fully regenerating the solid cyclodextrin.

The separation process herein may be carried out in the complete absence of water or alternatively conducted in the presence of a small concentration of water, but insufficient water to dissolve the cyclodextrin.

Preferably, the molecular species to be separated are organic compounds, most preferably linear or branched alkanes, cycloalkanes, alkenes, dienes of benzenes. It is also preferred that the cyclodextrin contain at least six glucose units, preferably 6-8 glucose units, and have a well-ordered cage lattice as described further hereinbelow.

It is noted that "sorption" as used herein is a generic term referring to any means by which the molecular species are taken up by the cyclodextrin or derivative thereof, including both absorption and adsorption processes. Thus, by use of the word "sorption" no distinction is being made between uptake of liquid versus gaseous molecular species, or between uptake by condensation on the surface of the cyclodextrin versus uptake by penetration into the cyclodextrin, or between uptake by complexation of species in the cyclodextrin cavity versus uptake by unlocalized dissolution of species in the solid cyclodextrin.

Applications in which the cyclodextrins herein are particularly useful include packed bed sorption, separations using magnetically stabilized fluidized beds, continuous chromatography, and gas and liquid chromatography.

BRIEF DESCRIPTION OF THE DRAWINGS

FIG. 1 is a pictorial representation depicting the chemical structure of the monomeric alpha-cyclodextrin oligosaccharide containing six glucose monomers.

FIG. 6 is a pictorial representation of the cage-type lattice configuration of the alpha-cyclodextrin hexahydrate structure.

FIG. 7 graphically illustrates the separation of four butene isomers and 1,3-butadiene from a mixture thereof achieved on an alpha-cyclodextrin gas chromatography column at 0° C.

DESCRIPTION OF THE PREFERRED EMBODIMENTS

The mixture of components to be separated by the process herein must contain at least two different molecular species, but no upper limit is placed on the number of different types of molecular species which may be contained therein. The molecular species in the mixture may differ widely in size and shape or may be of very similar structure, as in the case of isomers. For purposes of this invention, all of the molecular species in the mixture must be in the fluid (i.e., liquid and/or gaseous) states, including solutions of solids in liquids or vapors of species that are more commonly found in solid or liquid form. Suitable such molecular species include organic compounds such as, e.g., hydrocarbons, ketones, ethers, alcohols, esters, halogenated hydrocarbons, and the like; inert gases such as helium, argon and neon; inorganic species such as nitrogen, water, carbon dioxide, and ammonia; organometallic compounds such as ferrocene; and mixtures of any of the above. Organic compounds, including isomers, are particularly preferred. Representative of the organic compounds contemplated herein for use are, e.g., linear and branched alkanes, preferably $C_1$–$C_{10}$ alkanes, alkenes, dienes, alkynes, unsubstituted and substituted benzene and its derivatives, dialkyl ethers, alkanones, chlorinated hydrocarbons, etc. Especially useful practical applications of the separation process herein include separation of high octane-rating components of naphtha, removal of 1-butene or cycloolefins from alkylation feed, separation of the most highly branched, highest octane-rating alkylation products, separation of chemical feeds and products, and quantitative analysis of petroleum components according to molecular shape.

The cyclodextrin utilized in the process of this invention is a monomeric torus-shaped oligosaccharide composed of alpha-1,4-linkages, preferably of at least six glucose units, most preferably 6-8 glucose units, wherein a Greek letter denotes the number of units, e.g. alpha for 6, beta for 7, gamma for 8, etc.

A pictorial representation of the chemical structure of the decomplexed alpha-cyclodextrin molecule (six glucose units) is depicted in FIG. 1. Six primary hydroxyl groups lie on one side of the torus and twelve secondary hydroxyl groups on the other side. In known crystal structures, the central cavity of the molecule is slightly "V" shaped, with the secondary hydroxyl side more open than the primary hydroxyl side. The cavity is lined with non-polar groups and has a suitable free diameter of 5 angstroms for binding not only alkanes, but also aromatic compounds and other molecules of similar size. Beta-cyclodextrin and gamma-cyclodextrin with seven and eight glucose units, respectively, have a similar torus structure but with a larger central hole (6–8 angstroms) to accommodate branched compounds and compounds of larger size.

Figure 2:
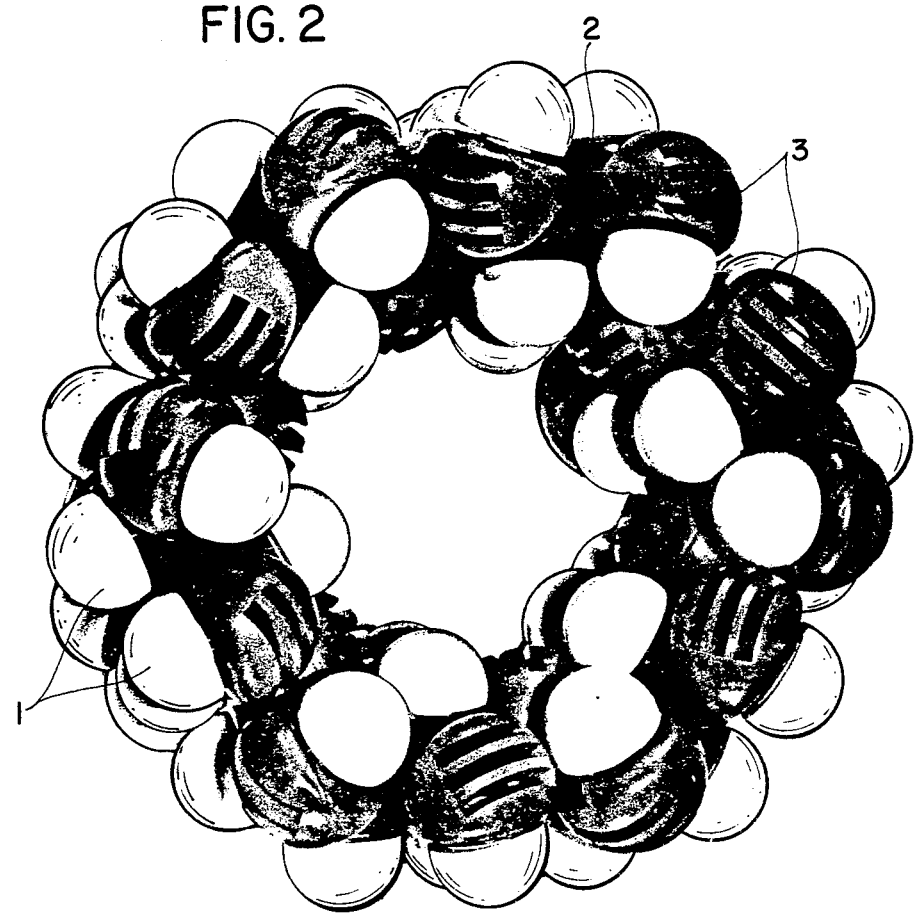
FIG. 2 is a space-filling molecular model depicting the torus structure of the alpha-cyclodextrin oligosaccharide containing six glucose monomers.

A molecular model for the structure of the decomplexed alpha-cyclodextrin molecule is depicted in FIG. 2. The hydrogen atoms 1 in the cyclodextrin are bonded to carbon atoms 2 and also to oxygen atoms 3.

Figures 3, 4:
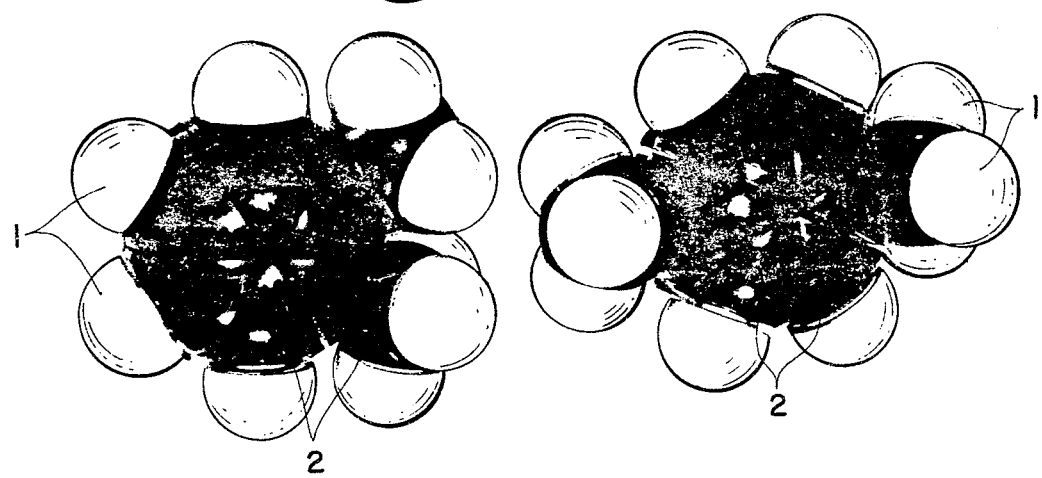
FIG. 3 is a space-filling molecular model depicting the structure of para-xylene.
FIG. 4 is a space-filling molecular model depicting the structure of ortho-xylene.
Figure 5:
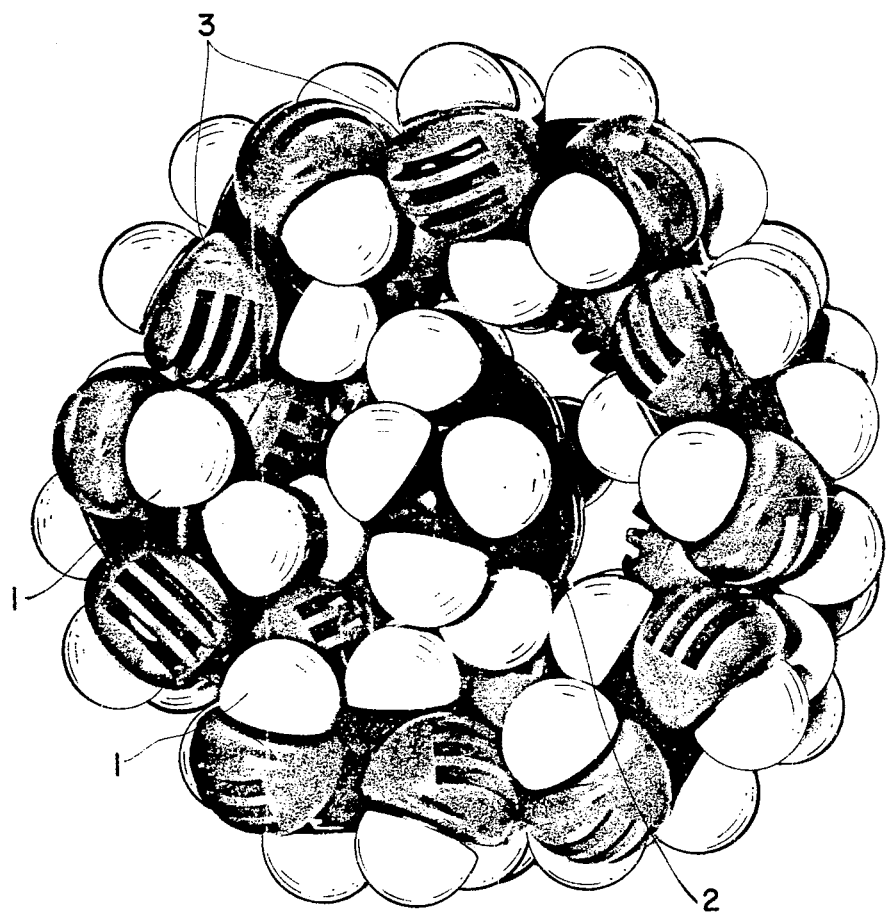
FIG. 5 is a space-filling molecular model depicting the structure of an inclusion complex of alpha-cyclodextrin with para-xylene.

FIGS. 3 and 4 depict molecular models of p-xylene and o-xylene, respectively, wherein the hydrogen atoms 1 are connected to carbon atoms 2. These xylenes are aromatic isomers differing only in the relative locations of two methyl groups on the benzene ring. A molecular model of the complex of alpha-cyclodextrin with p-xylene is given in FIG. 5, wherein hydrogen atoms 1 are bonded to carbon atoms 2 and oxygen atoms 3. It is seen that p-xylene is comfortably accommodated in the non-polar cavity of the alpha-cyclodextrin; o-xylene is also accommodated in the non-polar cavity but somewhat more tightly.

By the words "solid particulate cyclodextrin" is meant cyclodextrin in the solid phase and in particulate form which is not dissolved to an appreciable degree in a solvent when contacted with the molecular species or when desorbing or sorbing the molecular species. Although the solid cyclodextrin need not be in crystalline form, crystalline materials are preferred herein. Among the crystalline cyclodextrins which are particularly preferred are included those having a high degree of order in the crystal lattice rather than those with less perfectly ordered crystal lattices or those comprising mixtures of ordered and disordered lattices.

Cyclodextrins are known to crystallize in two general lattice types, i.e., cage and channel lattices. In channel lattices the cyclodextrin toruses are stacked directly on top of each other, forming continuous, approximately cylindrical channels similar to those found in zeolites. In cage lattices, on the other hand, the cyclodextrin toruses lie at angles to one another or are stacked in brickwork fashion so that there are no obvious continuous channels which would be receptive to guest molecules. While the cyclodextrin herein, if crystalline, may have a cage or channel lattice, particularly notable results are achieved when a crystalline cyclodextrin in cage lattice form is employed. FIG. 6 depicts the cage lattice arrangement, wherein each alpha-cyclodextrin torus 4 contains a cavity 5 enclosed by dashed lines.

The cyclodextrin applicable herein may be underivatized or derivatized by converting one or more hydroxyl groups of the cyclodextrin to another functional group. Examples of suitable cyclodextrin derivatives include ethers, esters such as acetates, thiols, carbamates, and the like, many of which are already known. It should be noted, however, that in all cases the term "cyclodextrin" as used herein applies only to monomeric cyclodextrin and therefore does not encompass polymerized or copolymerized cyclodextrins or cyclodextrins crosslinked with one another.

Preparation of the cyclodextrins of this invention may be achieved by any route desired by the practitioner. A typical preparation procedure involves fermentation, derivatization, if applicable, and subsequent crystallization of the cyclodextrin product from an aqueous or partially aqueous solution thereof. During crystallization the aqueous solvent and/or other solutes or co-solvents are complexed as guest molecules within the cyclodextrin to form a stable, hydrated inclusion complex therewith such as, e.g., alpha-cyclodextrin hexahydrate or alpha-cyclodextrin etherate hydrate. The wet filter cake of the product obtained on filtration from the mother liquor may be employed directly in the separation, during which any remaining surface liquid will be evaporated to form the crystalline material in situ. As this in situ drying procedure results in slower sorption and separation rates, it is preferred to drive off the surface liquid from the wet cake prior to use, as by, for example, drying in an oven or in vacuo. The extent of drying employed for this purpose depends on the drying means used, the type of cyclodextrin, and the rate of separation desired, with more extensive drying tending to remove the guest species from the inclusion complex.

The degree of separation achieved by the process herein is somewhat dependent on the surface area of the cyclodextrin, with increased surface area (i.e., reduced particle size) corresponding to improved sorption. Smaller particles obtained directly by rapid crystallization of the cyclodextrin through, e.g., stirring or rapid cooling consist of less ordered crystals which adversely affect separation results. It is therefore preferred, if the cyclodextrin is dried, to grind the large well-ordered crystals obtained by slow crystallization to a smaller size and to pass the resulting material through a sieve so as to reduce the particle size of the cyclodextrin to within a desirable range. This sieving process is particularly preferred when the cyclodextrin is to be employed as a stationary phase in chromatographic techniques. The optimal particles size will vary considerably with the type of cyclodextrin and molecular species to be separated, but is preferably no greater than about 1 mm, and most preferably no greater than about 0.1 mm. The particles may be of any shape, e.g., spherical, irregular shaped or elongated.

Consistent with effectuating a successful separation by the process herein, the cyclodextrin is necessarily capable of reversibly sorbing at least one of the molecular species to be separated and capable of sorbing or desorbing one such molecular species to a greater extent than others. The cyclodextrin may contain complexed molecular species other than those in the mixture to be separated, which species may be included as guests within the cavity of the cyclodextrin host and/or may occupy interstitial lattice sites between cyclodextrin molecules. For example, the alpha-cyclodextrin hexahydrate may be employed in complexed form. If, however, the cyclodextrin is so saturated with such complexed species that it cannot sorb any additional molecular species, then it is not useful in the separation process herein. In those instances where it is necessary or desirable to activate these complexes by partially or fully desorbing the complexed species therefrom, an additional treatment of the cyclodextrin is carried out. For this purpose, the crystalline complex may be maintained at room temperature and atmospheric pressure for a sufficient period of time to allow desorption of the complex. While the particular mode of desorption depends on the type of cyclodextrin complex involved, in a preferred embodiment the complex is activated by applying heat thereto under atmospheric or reduced pressure or under a flow of inert gas. If elevated temperatures are employed, they should generally not exceed about 230° C., depending on the pressure applied, the particular type of complex and the length of the heating period, as the complexes tend to discolor, decompose and/or melt when exposed for relatively short periods to higher temperatures. In a particularly preferred aspect of the invention the complex is activated by heating at about 150°–175° C. in vacuum or under an inert gas flow for at least about 15 hours.

In the first step of the process herein the solid particulate monomeric cyclodextrin is contacted with a mixture of the molecular species to be separated. The particular separation technique employed is not critical to the invention. Thus, any separations involving interactions of solid-liquid or solid-gas phases may be utilized, including analytical chromatography such as gas or liquid chromatography on a cyclodextrin stationary phase, separations via magnetically stabilized fluidized beds such as described in U.S. Pat. Nos. 4,247,987 and 4,283,204, continuous chromatography using a simulated moving bed as described by R. W. Neuzil, et al., *Chemtech*, 498(1980), packed bed sorption, and the like. For small-scale separations, gas chromatography represents a preferred technique because it is a fast and extremely sensitive means of separation which can be automatically recorded by detectors. For industrial-scale operations, packed bed sorption and continuous chromatography in magnetically stabilized fluid beds are the preferred procedures.

If the cyclodextrin is to be employed in magnetically stabilized beds, it must first be admixed with a magnetizable component and a magnetic field must be applied to stabilize or structure the bed before the contacting step as described in U.S. Pat. Nos. 4,247,987 and 4,283,204, the disclosures of which are incorporated herein by reference. The bed of particles is then countercurrently contacted with the mixture of molecular species to be separated.

The exposure of the mixture of molecule species to the solid particulate cyclodextrin is preferably carried out under conditions wherein the cyclodextrin is not appreciably dissolved in a liquid phase. Thus, the mixture may be contacted with the cyclodextrin in the complete absence of such liquid phase or in the presence of small concentrations of such liquid phase provided that the amounts are insufficient to dissolve the cyclodextrin. It will be recognized, however, that water-soluble cyclodextrins should not be exposed to liquid water, either per se or as condensed water vapor, in which they will dissolve.

The process operating conditions to be employed in the practice of the present invention may vary widely and will include those treating conditions typically employed in the sorption-desorption separation processes known in the art. As well known, these conditions will generally vary depending on the type of separation system and cyclodextrin utilized, the nature of the molecular species to be separated, etc. The conditions ordinarily utilized in separations using magnetically stabilized beds are specified by U.S. Pat. Nos. 4,247,987 and 4,283,204. In general, the temperatures used for sorption will be those at which one or more species are preferentially sorbed onto the particular cyclodextrin employed.

As an example, in gas chromatographic separations of liquid organic compounds using alpha- or beta-cyclodextrins, good results are often achieved at a column temperature maintained at about 30° C., although elevated temperatures up to about 175° C. are still effective in resolving the mixture into its component parts. Other systems will require lesser or greater temperatures for optimal separations, and in some cases programmed temperature control whereby the temperature is increased with time at a preset rate may be effective. In this regard it will be recognized that lower temperatures tend to enhance the degree of sorption of the molecules on the cyclodextrin, whereas higher temperatures promote desorption of the molecular species, shortening retention times to a point at which temperature no resolution whatsoever is obtained. In other separation techniques the temperature and other parameters of the system may need to be altered to create a differential between conditions of sorption and desorption sufficient for the cyclodextrin to release its guest molecules separately. In general, however, the temperatures found to be effective for separations using cyclodextrins are frequently lower than those effective for separations using zeolites.

Desorption of the species may generally be effected not only by increasing the temperature of the system but also by decreasing partial pressure of the sorbed species and/or by adding to the system an excess of a desorbent species defined as a material sorbing slightly less strongly than the sorbed species but of sufficiently different structure so that the sorbed species and desorbent species can be readily separated from each other as by distillation. When the excess amount of desorbent species displaces the sorbed species on the complex, the residual amount of desorbent is driven off and separated from the sorbing species.

Besides temperature and pressure, other important factors to consider for sorption-desorption operations include, in chromatographic separations, carrier gas or liquid flow rate, concentration of the injected sample, column length, and particle size of the cyclodextrin, and, in magnetically stabilized bed separations, the rate of movement of the bed particles, etc., The objective is to optimize these parameters such that the best resolution and separation of the components is achieved, an objective which is well within the skill of the practitioner.

In chromatographic separations the separate sorption on or desorption from the cyclodextrin of each molecular species ordinarily occurs as the components of the mixture are moved by the liquid or gaseous carrier through the column or sorption bed and are selectively sorbed and removed according to their molecular shapes. With gas chromatography the components sorbed most strongly will have the longest retention time (i.e., time between injection of sample and emergence of component from column), while those sorbed to a lesser degree will be eluted first. Elution order of the components in the mixture is indicative of the shape selectivity of the cyclodextrin. Non-selectivity is indicated by elution in order of increasing boiling points.

It is noted that the direction of selectivity of the cyclodextrin for the components, i.e., the order in which the components are sorbed or desorbed, is dependent on several factors relating to the type of cyclodextrin employed, one factor being the number of glucose monomers therein. Thus, the narrow channel of the alpha-cyclodextrin tends to sorb compact molecules, such as normal alkanes, more strongly than bulkier species, e.g., branched alkanes and aromatic compounds. The more accommodating channel of beta-cyclodextrin exhibits an inverse order of selectivity tending to sorb bulkier molecules preferentially. Another factor affecting the order of selectivity is the lattice structure of the cyclodextrin. For example, different selectivities are observed with sorbents obtained by drying alpha-cyclodextrin hexahydrate versus those obtained by drying alpha-cyclodextrin etherate hydrate. In addition, chemical derivatization of the cyclodextrin hydroxyl groups may have an effect on the order of selectivity. While the direction of selectivity generally appears to be independent of crystal quality, the magnitude of sorption and the retention time of the components are dependent on the degree of disorder within the crystalline lattice. Thus, as noted above, slowly crystallized cyclodextrins generally display a greater degree of sorption than cyclodextrin crystals having the same number of glucose units produced by rapid crystallization from the same solvent.

With gas chromatography, isolation of the separated components may be accomplished by several techniques. The solute vapors may be collected as separate fractions in a cold trap as they emerge from the column, where a detector indicates their appearance. Alternatively, the packing may be forced out of the column and cut into sections, each of which is treated with a solvent which would cause the component to be desorbed. In still another mode of operation the column may be washed with sufficient solvent or with a succession of solvents until each of the sorbed components has been eluted in turn and collected. The recovery of the components using other separation techniques may be accomplished using procedures which are well known to those skilled in the art.

The invention is further illustrated by the following examples, which, however, are not to be taken as limiting in any respect. All parts and percentages, unless expressly stated to be otherwise, are by weight.

EXAMPLE 1

This example illustrates the preparation of hydrated complexes of alpha- and beta-cyclodextrins (referred to herein for brevity as alpha-CD.H$_2$O and beta-CD.H$_2$O, respectively) for use in the present process.

Aqueous solutions nearly saturated with either alpha-CD or beta-CD and having an initial temperature as indicated in Table 1 were cooled to either 25° C. or 0° C. under the conditions indicated in the table to form crystals of various sizes designated as A–E. It can be seen that crystal size was controlled by varying the initial and final solution temperatures, the cooling rates, and the stirring of the solutions. Each precipitate was recovered by filtration and subsequent drying for about two hours in a vacuum. The products were ground to the desired particle size and then passed through a sieve.

The structures of the inclusion complexes obtained were identified with the cage lattices reported by B. Klar, et al, *Acta Cryst.*, B36, 1154 (1980) and K. Lindner, et al., *Angew. Chem. Int. Ed. Engl.*, 17, 694 (1978) by comparison of unit cell dimensions. Elemental analysis and weight loss upon dehydration at 175° C. in vacuum approximately confirmed the reported stoichiometries of alpha-CD.6H$_2$O and beta-CD.12H$_2$O. The breadth of X-ray powder diffraction lines indicated that the more rapidly crystallized materials had somewhat disordered crystal structures.

TABLE 1

| Type of Inclusion Complex | Designation of Complex | Solution Temperature (°C.) Initial | Solution Temperature (°C.) Final | Cooling Rate | Stirring | Crystal Size (mm) |
| --- | --- | --- | --- | --- | --- | --- |
| alpha-CD.H$_2$O | A | 50 | 25 | ca 5 hours | no | 1–10 |
| alpha-CD.H$_2$O | B | 100 | 0 | plunged into ice bath | no | 0.01–0.1 |
| alpha-CD.H$_2$O | C | 100 | 0 | plunged into ice bath | yes | 0.005–0.03 |
| beta-CD.H$_2$O | D | 95 | 25 | ca 5 hours | no | 1–10 |
| beta-CD.H$_2$O | E | 100 | 0 | plunged into ice bath | no | 0.01–0.1 |

EXAMPLE 2

This example illustrates the preparation of inclusion complexes of alpha-cyclodextrin with ether (for brevity referred to as alpha-CD.Et$_2$O.H$_2$O) for use in the process herein.

Four complexes of various crystal sizes were prepared by layering ether over a nearly saturated aqueous alpha-cyclodextrin solution at room temperature or by exposing the aqueous solution to ether vapors. The conditions controlling crystal size are indicated in Table 2. The resulting precipitates were filtered, washed with ether or with cold water, and dried for about one hour in vacuum, whereupon they were ground to the desired size and passed through a sieve. A similar preparation procedure was reported to give a channel-type lattice of unknown stoichiometry by R. K. McMullan et al., *Carbohydrate Research*, 31, 37 (1973). Elemental analysis indicated that most of the ether had desorbed from the products upon drying thereof, although residual ether was clearly visible in a solid state $^{13}$C-NMR spectrum of the product.

TABLE 2

| Designation of alpha-CD.Et$_2$O Complex | Volume of Aqueous Solution (ml) | Ether Exposure | Stirring | Crystal Size (mm) |
| --- | --- | --- | --- | --- |
| F | ca 300 | liquid layer | no | 1–20 |
| G | ca 10 | vapor | no | ca 4 |
| H | ca 10 | liquid layer | no | ca 0.4 |
| J | ca 10 | liquid layer | yes | 0.01–0.1 |

EXAMPLE 3

This example illustrates the reversible sorption properties of the inclusion complexes herein.

An approximately 7 mg sample of hydrated complex C or of etherate hydrate complex J was placed in the pan of a thermogravimetric analyzer. About 7% of the weight of each sample was lost upon heating to 215° C. under an argon purge. Cooling to 34° C. resulted in an argon uptake of 0.4% by weight in each sample over an approximately one-hour period. The weight gain of each sample was entirely reversed by reheating to 215°

C. The weight gain and loss of Sample J were qualitatively reproduced through three similar temperature cycles.

EXAMPLE 4

This example illustrates the shape selectivity for various organic compounds in the process herein.

Hydrated complex B, etherate hydrate complex J and hydrated complex E, all screened to 60− mesh, were packed into stainless steel gas chromatography columns of 0.085 in (0.22 cm) internal diameter by 20 in (50.8 cm) length. Each column was heated at 200° C. for two hours under a helium carrier flow rate of 20 ml/min. Substantial amounts of material (presumably water and ether) were eluted from the columns at the beginning of the heat treatment. A control column was similarly packed with an inert non-sorbent material commonly employed as a solid support in gas chromatography made from diatomaceous earth of 100/120 mesh which has been washed with acid and treated with dimethyldichlorosilane, and heat-treated.

Separate 0.3 μl samples of solutions of several hydrocarbons indicated in Table 3, each 1.00% by volume in pentane, were injected into each of the four columns, maintained at the indicated temperatures. Retention times of each hydrocarbon were measured for each column with a thermal conductivity or flame ionization detector. Shape selectivity of the cyclodextrin in each column was indicated by the failure of retention times to correspond to the order of boiling point. The inert control column retained the higher boiling compounds only slightly and eluted all compounds in order of boiling point.

It is noted that retention times within any group of structurally similar molecules were still influenced by boiling point; however, the less similarly structured compounds were not eluted in the order of their respective boiling points from the cyclodextrin columns. It is also observed that retention times were reduced with increasing column temperature. Hydrated complexes B and E having cage lattices showed unexpectedly good selectivity in view of their restricted cage structures.

at 175° C. for 18 hours under helium carrier flow to dehydrate the complex. About 10 microliters of an approximately equimolar gaseous mixture of 1-butene, cis-2-butene, trans-2-butene, 2-methylpropene and 1,3-butadiene was injected into the column at 0° C. at a carrier flow rate of 20.9 ml/min. The chromatogram shown in FIG. 7 was obtained. Each of the components of the mixture exhibited a peak and was thus capable of separation from the mixture such as by means of a cold trap. As controls, a 0.085 in (0.22 cm) by 12 in (30.5 cm) zeolite 13X column and a 0.085 in (0.22 cm) by 72 in (183 cm) zeolite 5A column contacted with the same mixture failed to elute the olefins below temperatures of about 200° C.

EXAMPLE 6

A gas chromatography column packed with hydrated complex D of 80/100 mesh (0.085 in (0.22 cm) by 72 in (183 cm)) and a gas chromatography column packed with hydrated complex A of 200/325 mesh (0.085 in (0.22 cm) by 12 in (30.5 cm)) were dehydrated by heating at 175° C. for 18 hours under helium carrier flow.

Figure 8:
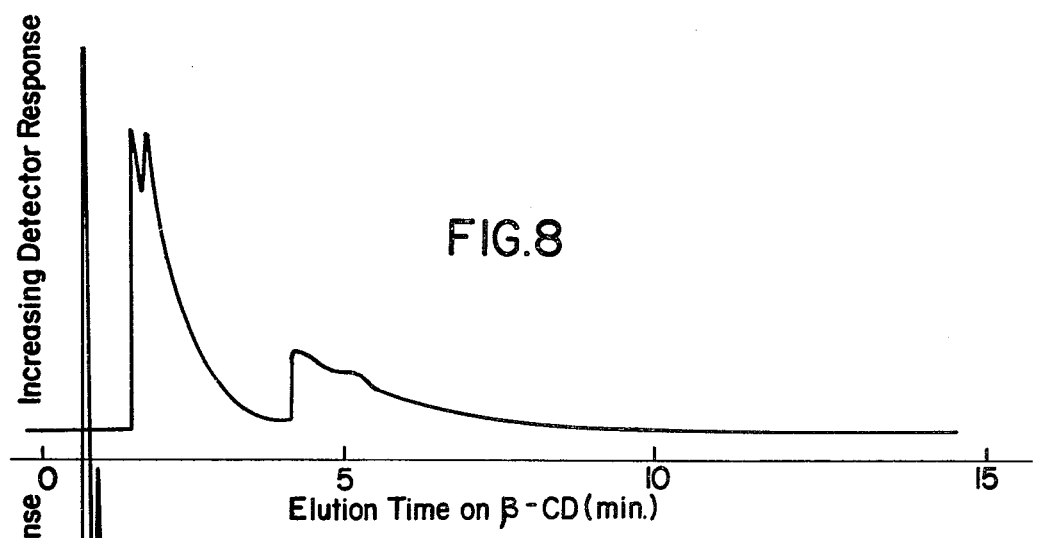
FIG. 8 graphically illustrates the degree of separation of closely boiling aliphatic compounds achieved on a beta-cyclodextrin gas chromatography column at 60° C.
Figure 9:
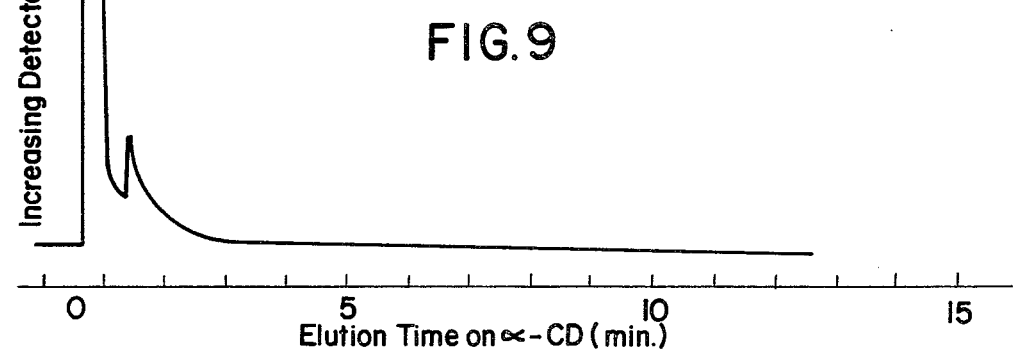
FIG. 9 graphically illustrates the degree of separation of closely boiling aliphatic compounds achieved on an alpha-cyclodextrin gas chromatography column at 26° C.

A 10–25 microliter sample of the vapor in equilibrium with an approximately equimolar mixture of five close-boiling linear, branched and cyclic alkanes was injected into the complex D column, maintained at 60° C. with a 30 ml/min helium carrier rate, and into the complex A column, maintained at 26° C. with a 29.3 ml/min. helium carrier rate. Table 4 indicates which compounds are in the mixture, their diameters and boiling points, and their retention times as deduced by injecting the pure compounds and mixtures omitting one or more of the five compounds into the columns. The observed retention times corresponded more closely with molecular shape than with boiling point; for example, complex A retained compounds with small critical diameters most strongly. FIGS. 8 and 9 depict the chromatograms for complexes D and A, respectively, showing a definite separation of the components. (Note that complex A did not elute heptane in the time shown.)

Two additional 10–25 microliter vapor-phase samples

TABLE 3

| Hydrocarbon | Boiling Point (°C.) | Complex B | | | Retention Time (min.) | | |
| --- | --- | --- | --- | --- | --- | --- | --- |
| | | 30° C. | 50° C. | 75° C. | Complex J 30° C. | Complex E 30° C. | Control 30° C. |
| Pentane (solvent) | 36 | 0.37 | 0.31 | 0.29 | 0.33 | 0.14 | 0.12 |
| Cyclopentane | 50 | NR* | ** | NR | NR | NR | NR |
| Cyclohexane | 81 | 0.75 | ** | NR | 0.49 | NR | NR |
| 3-Methylhexane | 91 | 3.58 | ** | 0.50 | 1.08 | 0.29 | NR |
| 2,2,4-Trimethyl-pentane | 98 | 2.26 | ** | 0.48 | 1.09 | 0.39 | NR |
| Heptane | 98 | 11.35 | ** | 0.77 | 1.56 | 0.35 | NR |
| Toluene | 111 | 5.06 | 2.22 | 0.72 | 1.72 | 1.06 | NR |
| cis-1,3-Dimethyl-cyclohexane | 120 | 3.46 | ** | 0.59 | 1.51 | 0.38 | 0.17 |
| Octane | 126 | >24 | ** | 1.84 | 4.28 | 0.78 | 0.20 |
| p-Xylene | 138 | 17.61 | ca 7.4 | 1.51 | 5.33 | 1.12 | 0.23 |
| m-Xylene | 139 | 16.59 | 6.44 | 1.39 | 5.48 | 1.01 | 0.23 |
| o-Xylene | 144 | 13.95 | 5.34 | 1.21 | 5.08 | 2.29 | 0.24 |

*NR = peak not resolved from pentane
** = not determined

EXAMPLE 5

This example illustrates separation of olefins using the process of this invention.

Figure 10:
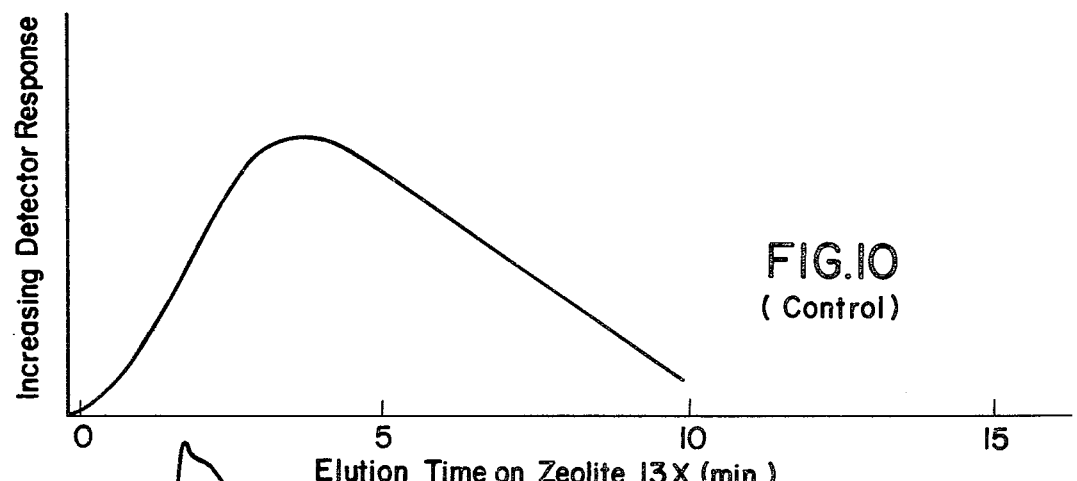
FIG. 10, representing a control, graphically illustrates the degree of separation of closely boiling aliphatic compounds achieved on a zeolite 13X gas chromatography column at 275° C.
Figure 11:
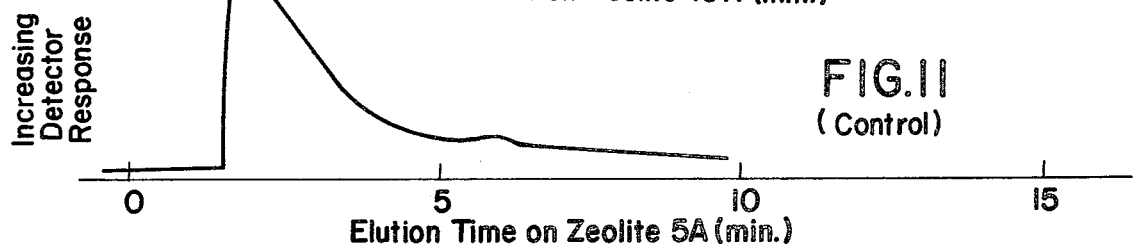
FIG. 11, representing a control, graphically illustrates the degree of separation of closely boiling aliphatic compounds achieved on a zeolite 5 A gas chromatography column at 100° C.

A gas chromatography column of 0.085 in (0.22 cm) internal diameter by 12 in (30.5 cm) length was packed with hydrated complex A of 200/325 mesh and heated of the mixture were injected into a 0.085 in. (0.22 cm) by 12 in. (30.5 cm) column of zeolite 13X of 80/100 mesh maintained at 275° C. with a 35.2 ml/min helium carrier flow, and also into a 0.085 in. (0.22 cm) by 72 in. (183 cm) column of zeolite 5A of 80/100 mesh maintained at 100° C. with a 40 ml/min helium carrier flow rate. The chromatograms for zeolite 13X and zeolite 5A are respectively shown in FIGS. 10 and 11. The zeolite 13X column required very high temperatures for elution and still did not separate the mixture. The zeolite 5A column did not elute heptane in the time shown, but did not separate the other components of the mixture nearly as well as did the cyclodextrins.

none of the other compounds except carbon tetrachloride.

A 25 microliter vapor-phase sample of a heptane/methanol mixture was separated on this gas chromatography column at 110° C. and 7.3 ml/min helium flow rate. Retention times for heptane and methanol were 0.45

TABLE 4

| Hydrocarbon | Critical Diameter (Å)** | Boiling Point (°C.) | Retention Time (Min) Complex A | Retention Time (Min) Complex D |
|---|---|---|---|---|
| 2,3-Dimethylpentane | 6.5 | 90 | 0.72 | 1.79* |
| 3-Methylhexane | 5.6 | 91 | 1.49 | 1.58* |
| Heptane | 5.0 | 98 | >20 | 1.79* |
| 2,2,4-Trimethylpentane | 6.2 | 98 | 0.99 | 4.26*** |
| 1-Methylcyclohexane | 6.5 | 101 | 0.72 | 5.20*** |

*Probable assignments. 3-Methylhexane may elute at 1.79 min. and the other two compounds at 1.58 min.
**Defined as the diameter of the smallest cylinder of infinite length that can include the hydrocarbon in any reasonably stable conformation, and determined from spacefilling molecular models.
***These assignments may be inverted.

EXAMPLE 7

This example illustrates the separation of components by cyclodextrin in the presence of water vapor.

The gas chromatography column packed with complex A described in Example 6 was equilibrated for 24 hr at 30° C. with a 30 ml/min flow of helium carrier gas containing 250 ppm by volume of water vapor. A 25 microliter sample of the vapor in equilibrium with a mixture of 100 microliters of heptane and 10 microliters each of 2,3-dimethylpentane, 3-methylhexane, 2,2,4-trimethylpentane, and 1-methylcyclohexane was injected into the moist carrier gas stream. Retention times for each compound in the mixture, established by injecting the pure components and all possible mixtures of four components at a time, were 0.95, 0.26, 0.64, 0.38, and 0.26 min, respectively. It will be noted that the order of elution from the column was the same as that with dry carrier gas (Example 6) but that retention times are somewhat reduced.

EXAMPLE 8

This example illustrates use of an amorphous cyclodextrin derivative in the separation process herein.

Beta-cyclodextrin was fully acetylated by the method reported by D. French in *Adv. Carbohydrate Chem.*, 12, 189 (1957). The product, recrystallized once from toluene and dried in vacuum at ca. 90° C., was amorphous by X-ray powder diffraction. Elemental analysis and integration of the solid state $^{13}$C-NMR spectrum confirmed the theoretical composition of beta-cyclodextrin-(OAc)$_{21}$. No residual toluene was detected by elemental analysis or by NMR and IR spectroscopy.

The product was ground to 200/325 mesh, wet sieved with pentane, and packed in a 0.085 in (0.22 cm) by 12 in (30.5 cm) gas chromatography column. The column was conditioned at 120° C. for 18 hr under a 10 ml/min helium carrier flow. Table 5 lists retention times on this column of 25 microliter samples of vapor in equilibrium with several liquids at the same carrier flow rate and 30° C.

Retention times correlated neither with molecular size and shape nor with volatility, but rather with solubility of the derivative in each liquid. Thus, beta-cyclodextrin acetate is soluble in methanol, acetone, toluene, methylene chloride, chloroform, and 2-butanone, all of which gave long retention times, and in and 9.5 min, respectively.

TABLE 5

| Compound | Retention time (min) |
|---|---|
| heptane | 0.58 |
| 3-methylhexane | 0.47 |
| 2,3-dimethylpentane | 0.43 |
| 2,2,4-trimethylpentane | 0.50 |
| 1-methylcyclohexane | 0.49 |
| cyclohexane | 0.45 |
| carbon tetrachloride | 0.56 |
| diethyl ether | 0.35 |
| methanol | >20 |
| acetone | >20 |
| toluene | >20 |
| methylene chloride | >20 |
| chloroform | >20 |
| 2-butanone | >20 |

It is seen that use of monomeric cyclodextrins in solid particulate form, particularly crystalline cyclodextrins and most particularly those cyclodextrins having cage lattices, in the absence or presence of small amounts of water vapor, results in shape-selective separations of many branched alkanes and other similarly structured materials which zeolites cannot adequately separate or cannot separate at reasonably low temperatures.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. In a process for selectively separating two or more fluid molecular species from a mixture of the same wherein at least one molecular species is sorbed on a sorbent and the sorbed molecular species is then desorbed, thereby partially or fully regenerating the sorbent, the improvement which comprises employing as the sorbent an underivatized crystalline monomeric cyclodextrin containing 6–8 glucose units.

2. The process of claim 1 wherein said molecular species are selected from the group consisting of organic compounds, inert gases, inorganic compounds, organometallic compounds, and mixtures thereof.

3. The process of claim 1 wherein said molecular species are organic compounds.

4. The process of claim 3 wherein said molecular species are linear or branched alkanes, cycloalkanes, alkenes, dienes or benzenes.

5. The process of claim 1 wherein said cyclodextrin has a cage lattice.

6. The process of claim 1 wherein said cyclodextrin contains complexed molecular species other than those in the mixture to be separated.

7. The process of claim 6 wherein said complexed species is water.

8. The process of claim 1 wherein said cyclodextrin is free of complexed molecular species other than those in the mixture to be separated.

9. The process of claim 1 wherein said cyclodextrin is dried before contacting said mixture therewith.

10. The process of claim 1 wherein said cyclodextrin is crystallized in a well-ordered lattice form.

11. The process of claim 1 wherein said cyclodextrin is crystallized in an ordered lattice form, dried, and passed through a sieve to reduce its particle size before contacting said mixture therewith.

12. The process of claim 1 wherein said sorption step is carried out in the absence of water.

13. The process of claim 1 wherein said sorption step is carried out in the presence of water at a concentration insufficient to dissolve the cyclodextrin.

14. The process of claim 1 wherein said desorption step takes place by reducing the partial pressure of the sorbed species, by increasing the temperature, by adding a desorbent species which displaces the sorbed molecular species, or by any combination of these techniques.

15. The process of claim 1 wherein said steps take place by chromatography or packed bed sorption.

16. The process of claim 1 wherein said steps take place by gas chromatography.

17. The process of claim 16 wherein said steps take place at a temperature of no greater than about 175° C.

18. A process for selectively separating two or more molecular species selected from the group consisting of linear or branched alkanes, cycloalkanes, alkenes, dienes and benzenes from mixtures thereof comprising (1) contacting said mixture with a dried and sieved underivatized crystalline monomeric cyclodextrin containing 6-8 glucose units, (2) sorbing at least one molecular species on said crystalline cyclodextrin, and (3) desorbing said sorbed molecular species, thereby partially or fully regenerating the crystalline cyclodextrin.

19. The process of claims 1 or 18 wherein the regenerated cyclodextrin from the desorbing step is recycled for reuse in the contacting and sorbing steps.

* * * * *